Figure 1:
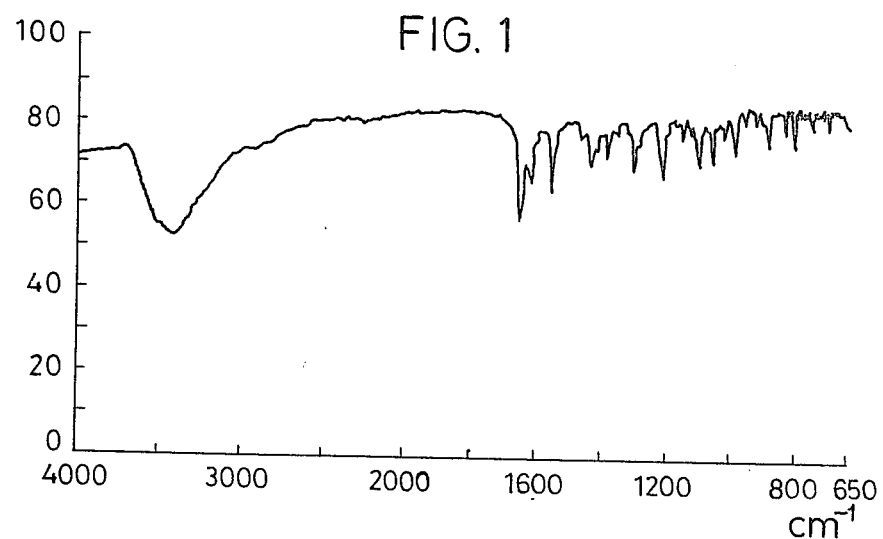

United States Patent [19]

Urakawa et al.

[11] 4,264,504
[45] Apr. 28, 1981

[54] MITOMYCIN DERIVATIVES

[75] Inventors: Chikahiro Urakawa, Machida; Masaji Kasai, Fujisawa; Haruko Tsuchiya, Ohtahara; Kunikatsu Shirahata; Kinichi Nakano, both of Machida; Itaru Takahashi, Kumamoto; Kazuyuki Mineura, Shizuoka, all of Japan

[73] Assignee: Kyowa Hakko Kogyo Co., Ltd., Tokyo, Japan

[21] Appl. No.: 58,670

[22] Filed: Jul. 18, 1979

[30] Foreign Application Priority Data

Jul. 18, 1978 [JP] Japan .................................. 53-86748

[51] Int. Cl.$^3$ .................... C07D 847/14; A61K 31/33
[52] U.S. Cl. .............................. 260/326.5 B; 424/274
[58] Field of Search .................................. 260/326.5 B Primary Examiner—Donald G. Daus
Assistant Examiner—D. B. Springer
Attorney, Agent, or Firm—Fitzpatrick, Cella, Harper & Scinto

[57] ABSTRACT

New mitomycin derivatives having antibacterial activity are produced by semi-synthetic processes and also by a fermentative method.

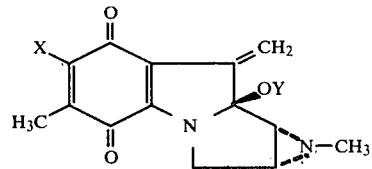

5 Claims, 4 Drawing Figures

MITOMYCIN DERIVATIVES

BACKGROUND OF THE INVENTION

This invention relates to new mitomycin derivatives and processes for production thereof.

As described in the Merck Index (Ninth Edition), the mitomycins are a complex of compounds having antitumor, antibiotic activity. Exemplary of the known mitomycins are those having the following structure and derivatives thereof.

|  | X | 9 | 10 | $R_A$ | $R_B$ |
|---|---|---|---|---|---|
| Mitomycin A | $OCH_3$ | ∥∥∥∥ |  | $CH_3$ | H |
| Mitomycin B | $OCH_3$ |  |  | H | $CH_3$ |
| Mitomycin C | $NH_2$ | .∥∥∥∥ |  | $CH_3$ | H |
| Mitomycin D | $NH_2$ |  |  | H | $CH_3$ |
| Mitomycin E | $NH_2$ |  |  | $CH_3$ | $CH_3$ |
| Porfiromycin | $NH_2$ | ∥∥∥∥ |  | $CH_3$ | $CH_3$ |

While the known mitomycins exhibit good activity, new antibacterial compounds are always in demand. To this end, the present inventors have found new mitomycin derivatives which have a double bond between the 9 and 10 positions and which have antibacterial activity.

SUMMARY OF THE INVENTION

In accordance with the present invention, mitomycin derivatives are produced having the general formula (I):

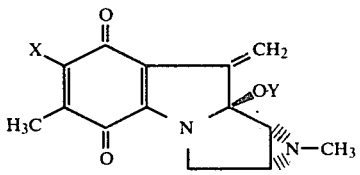

wherein X is an alkoxy group or an amino group, and Y is hydrogen or an alkyl group.

The invention also pertains to various semi-synthetic and fermentative processes for producing the compounds of the foregoing formula.

The compounds of the present invention have broad antibacterial activity and are, therefore, useful to clean and sterilizing laboratory glassware and surgical instruments, and may also be used in combination with soaps, detergents and wash solutions for sanitary purposes. The compound may also be useful as medicaments or intermediates in the preparation of other mitomycin derivatives having similar activity.

DESCRIPTION OF THE INVENTION

Compounds of the present invention are represented by the general formula (I):

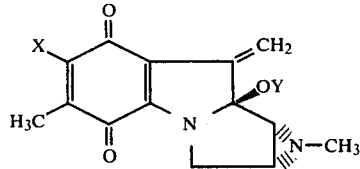

wherein X is an alkoxy group including a lower alkoxy group, such as methoxy, ethoxy, i-propoxy, n-butoxy, t-butoxy, and the like or is an amino group; Y is hydrogen or an alkyl group including a lower alkyl group, such as methyl, ethyl, n-propyl, i-propyl, n-butyl, i-butyl, t-butyl or the like.

Exemplary of these compounds are:

(1) 10-decarbamoyloxy-9-dehydro-mitomycin B (hereinafter referred to as Compound I);

(2) 9a-O-methyl-10-decarbamoyloxy-9-dehydro-mitomycin B (hereinafter referred to as Compound II);

(3) 7-amino-10-decarbamoyloxy-9-dehydro-7-demethoxy-mitomycin B (hereinafter referred to as Compound III); and (4) 7-amino-9a-O-methyl-10-decarbamoyloxy-9-dehydro-7-demethoxy-mitomycin B (hereinafter referred to as Compound IV).

Compounds I to IV correspond to the compounds of the above general formula wherein X and Y are the following groups and atoms.

|  | X | Y |
|---|---|---|
| Compound I | $OCH_3$ | H |
| Compound II | $OCH_3$ | $CH_3$ |
| Compound III | $NH_2$ | H |
| Compound IV | $NH_2$ | $CH_3$ |

Minimum inhibitory concentrations (m.c.g/ml) of these compounds against various bacteria are shown in Table 1.

TABLE 1

| Test Compound | Bacteria | | | |
|---|---|---|---|---|
|  | (a) | (b) | (c) | (d) |
| I | 0.782 | 0.098 | >50 | 12.5 |
| II | 6.25 | 0.391 | >50 | 12.5 |
| III | 3.125 | 0.098 | 25 | 3.125 |
| IV | 50 | 0.196 | >50 | 12.5 |
| V | <0.025 | <0.025 | 3.125 | 0.196 |
| VI | 3.125 | 0.782 | 25 | 3.125 |
| V | Mitomycin B | | | |
| VI | 7-amino-7-demethoxy-mitomycin B | | | |
| (a) | *Staphylococcus aureus* ATCC 6538P | | | |
| (b) | *Bacillus subtilis* No. 10707 | | | |
| (c) | *Shigella sonnei* ATCC 9290 | | | |
| (d) | *Klebsiella pneumoniae* ATCC 10031 | | | |

The compounds of the present invention may be produced by the following methods.

(A) A mitomycin derivative wherein Y is hydrogen in the general formula (I): namely a compound represented by the general formula:

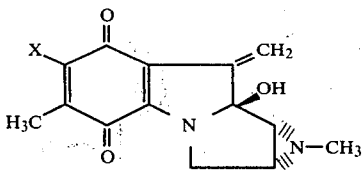

wherein X has the same meaning as defined above, is obtained by eliminating carbamic acid from a mitomycin represented by the general formula:

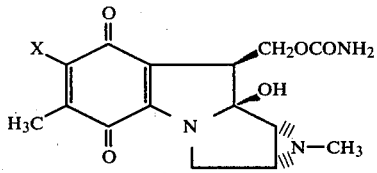

wherein X has the same meaning as defined above, in the presence of a base, and in a solvent inert to the reaction. The starting material is a known compound such as mitomycin B.

Suitable solvents for the reaction include tetrahydrofuran, dioxane, n-hexane, benzene, N,N-dimethylformamide, ethyl acetate, acetone, chloroform, and the like. Suitable bases for the reaction include sodium carbonate, sodium hydroxide, sodium hydride, triethylamine, potassium-t-butoxide, 1,5-diazabicyclo[5.4.0]undecene-5, and the like.

Typically, 1 to 30 times, preferably 1 to 10 times per mole of the base is used to the starting mitomycin. The reaction is generally carried out at $-80°$ to $70°$ C., preferably at $-30°$ to $50°$ C. The reaction time varies according to reaction temperature and the base used, but is usually 3 hours to 3 days.

After completion of the reaction, the desired compound is isolated and purified from the reaction solution by a conventional purification method such as that described in Examples 1 and 2.

(B) A compound wherein X in the general formula (I) is an amino group, namely a compound represented by the general formula

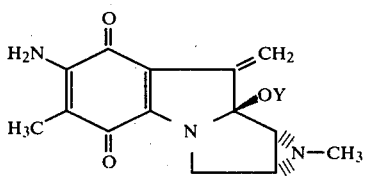

wherein Y has the same meaning as defined above, is obtained by reacting a compound represented by the general formula

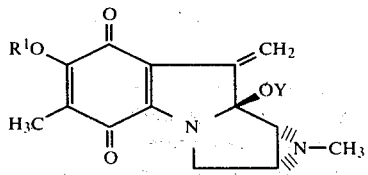

wherein $R^1$ is an alkyl group and Y has the same meaning as defined above with ammonia in an inert solvent.

The starting compound is a compound wherein X in the general formula (I) is an alkoxy group and is obtained by methods (A), (C) or (D). Suitable inert solvents for the reaction include ethanol, methanol, water, and the like.

Typically, 1 to $10^3$ times, preferably 1 to $10^2$ times per mole of ammonia is used to the starting mitomycin. The reaction is generally carried out at $-30°$ to $50°$ C., preferably at $0°$ to $30°$ C. and is generally completed in 1 to 48 hours.

After the completion of the reaction, the desired compound is isolated and purified from the reaction solution by a conventional purification method such as that described in Example 4.

(C) A compound wherein Y in the general formula (I) is an alkyl group, namely a compound represented by the general formula

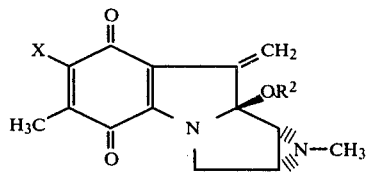

wherein X has the same meaning as defined above and $R^2$ is an alkyl group, is obtained by alkylating a compound represented by the general formula

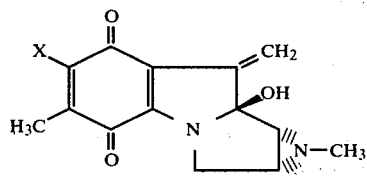

wherein X has the same meaning as defined above with an alkylating agent in the presence of a base and in an inert solvent.

The starting compound is a compound wherein Y is hydrogen in the general formula (I). As an alkylating agent, ethyl iodide, dimethyl sulfate, or the like may be used. Suitable bases and inert solvents are those mentioned in method (A) above.

The base and alkylating agent are typically employed in an amount of 1 to 50 times preferably 1 to 10 times per mole of the starting mitomycin. The reaction is generally carried out at $-30°$ to $50°$ C., usually at room temperature and is completed in a few seconds to 24 hours. Isolation and purification of the desired compound from the reaction mixture is carried out by the same method as in method (A) above.

(D) The compounds of the invention as represented by the general formula (I) may also obtained by culturing a microorganism belonging to the genus Streptomyces which is capable of producing such compounds in a nutrient medium, accumulating one or more of the compounds in the culture liquor and recovering the same therefrom. Any microorganism may be used so long as it belongs to the genus Streptomyces and is capable of producing a compound represented by the general formula (I). Preferably, a microorganism which belongs to the species Streptomyces caespitosus and has the ability to produce one or more of the compounds is employed such as *Streptomyces caespitosus* ATCC 27422. The microorganisms useful in carrying out the present invention can be mutated by artificial means such as ultraviolet irradiation, X-ray irradiation and use of various mutation inducing chemicals in known manner to enhance the production of metabolic products. Accordingly the present invention contemplates use of such mutants insofar as they have the ability to produce one or more of the desired compounds.

As the nutrient medium, any medium may be used so long as it contains an assimilable carbon source, nitrogen source, inorganic materials and other nutrients required by the particular strain. As a carbon source, glucose, fructose, blackstrap molasses, and the like may be used. As a nitrogen source, ammonia, ammonium phosphate, ammonium sulfate, ammonium acetate, urea, peptone, corn steep liquor, yeast extract, meat extract, dry yeast, etc. may be used. As inorganic materials, potassium hydrogen phosphate, sodium chloride, calcium carbonate, and the like are appropriate.

Culturing is carried out with shaking or by a submerged stirring culturing method. The culturing temperature is usually at 25° to 35° C. The pH of the fermentation medium is preferably maintained at about 6 to 8 but it is usually unnecessary to control this factor. Usually after 4 to 5 days culturing substantial antibacterial activity is detected in the culture liquor at which time culturing may be discontinued.

After the completion of culturing, recovery of the desired compound from the culture liquor may be carried out by those methods usually used for purification of an antibiotic, such as is described in Examples 5 to 7.

Certain specific embodiments of the invention are illustrated by the following representative examples.

EXAMPLE 1

Preparation of 10-decarbamoyloxy-9-dehydro-mitomycin B (Compound I)

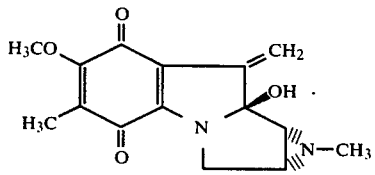

In this example, 100 mg of mitomycin B is dissolved in 5 ml of dioxane. To this solution, 100 mg of potassium t-butoxide is added and the mixture is stirred at room temperature for 2 days. The reaction mixture is then neutralized with an excess amount of dry ice and subjected to filtration. The filtrate is concentrated under reduced pressure and the residue is then subjected to silica gel column chromatography using a mixed solvent of acetone and chloroform (1:4) (volume ratio as is the same hereinafter) as a developer. Fractions of eluate which have a high Rf value and are blue are combined and concentrated under reduced pressure. The residue is crystallized from acetone and petroleum ether to obtain 14 mg of the desired compound (yield 17.0%) as purplish black needle-like crystals having the following physical properties.

(1) The compound exhibits molecular peak of $M^+ = 288.1086$ (calculated molecular weight is 288.1110 as $C_{15}H_{16}N_2O_4$) by high resolution mass spectrometry.

(2) The compound exhibits a purplish blue single spot of Rf value of 0.70 by silica gel thin layer chromatography (Art 5719 made by Merck & Co.) using a mixed solvent of acetone and chloroform (1:1) as the developer (Mitomycin B exhibits Rf value of 0.30 in the same condition).

(3) IR spectrum (KBr tablet) as is shown in FIG. 1.

(4) Chemical shift of proton by 60 MHz NMR using tetramethylsilane as internal standard and chloroform-D as a measuring solvent is shown by $\delta$(ppm): 6.32(s, 1H), 5.53(s, 1H), 3.00–4.20(1H), 2.27(2H), 2.18(s, 3H), 3.98(d, 1H), 3.45(d, 1H), 1.75(s, 3H), 4.05(s, 3H).

EXAMPLE 2

Preparation of 7-amino-10-decarbamoyloxy-9-dehydro-7-demethoxy-mitomycin B (Compound III)

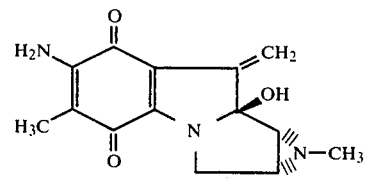

In this example, 1 g of 7-amino-7-demethoxy-mitomycin B and 3 g of silica gel (#7729 made by German Merck Co.) are added to 50 ml of tetrahydrofuran. To this mixture, 480 mg of sodium hydride (containing 50% of oil) is added with stirring and the mixture is stirred at room temperature for 2 days. Then, an excess amount of ethyl acetate saturated with water is added to decompose unreacted sodium hydride. An excess amount of dry ice is added to the mixture to neutralize the same. Then the mixture is subjected to filtration. The filtrate is concentrated under reduced pressure and the residue is subjected to silica gel column chromatography using a mixed solvent of acetone and chloroform (1:4) as a developer. Fractions of eluate which are eluted before unreacted starting material and are dark purplish green are combined and concentrated under reduced pressure to obtain 350 mg (yield 42.8%) of the desired compound as dark green needle-like crystals having the following physical properties.

(1) The compound exhibits molecular peak of $M^+ = 273.1118$ (calculated molecular weight is 273.1113 as $C_{14}H_{15}N_3O_3$) by high resolution mass spectrometry.

(2) The compound exhibits a yellowish green single spot of Rf value of 0.42 by the same silica gel thin layer chromatography as described in Example 1 (7-amino-7-demethoxy-mitomycin B exhibits Rf value of 0.10 in the same condition).

Figure 2:
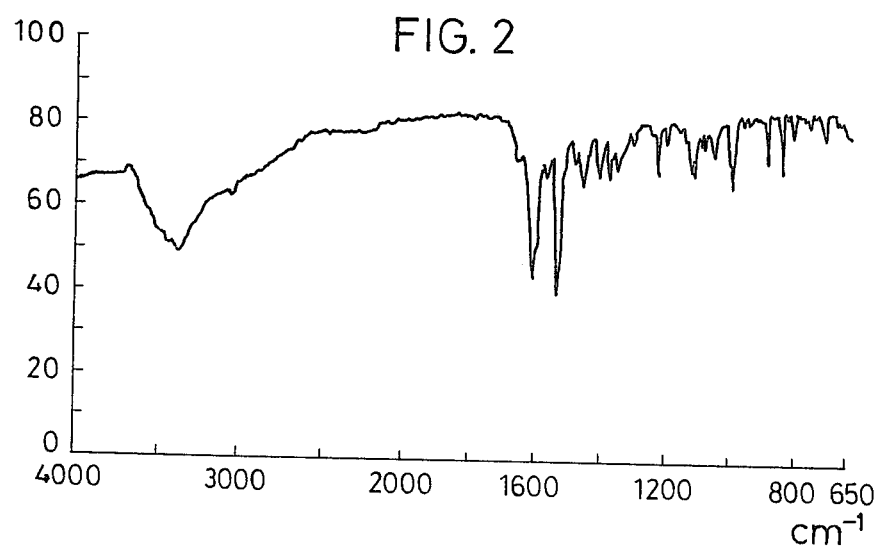

(3) IR spectrum (KBr tablet) as is shown in FIG. 2.

(4) Chemical shift of proton by 60 MHz NMR using tetramethylsilane as internal standard and a mixed solvent of chloroform-D and dimethyl sulfoxide-$D_6$ as a measuring solvent is shown by $\delta$(ppm): 5.90(s, 1H), 5.32(s, 1H), 6.33(s, 1H), 2.23(2H), 2.17(s, 3H), 4.22(d, 1H), 3.43(d, 1H), 1.70(s, 3H), 6.47(s, 2H).

EXAMPLE 3

Preparation of 9a-O-methyl-10-decarbamoyloxy-9-dehydro-mitomycin B (Compound II)

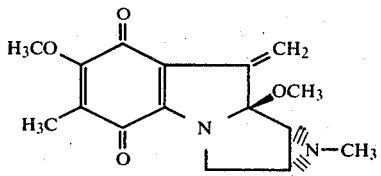

In this example, 20 mg of 10-decarbamoyloxy-9-dehydro-mitomycin B is added to a mixed solvent of 0.3 ml dimethylformamide and 1 ml benzene. To this mixture, 20 mg of sodium hydride (containing 50% of oil) is added with stirring. Then 0.035 ml of dimethyl sulfate is added to the mixture and the mixture is stirred for 2 minutes. Ethyl acetate saturated with water is added to the mixture to decompose unreacted sodium hydride. The mixture is then filtered and 10 ml ethyl acetate is added to the filtrate. The mixture is washed 5 times each with 2 ml of water. The organic layer is then dried with anhydrous sodium sulfate and concentrated under reduced pressure. The residue is subjected to silica gel column chromatography using a mixed solvent of acetone and chloroform (1:9) whereby 8.7 mg (yield 41.5%) of the desired compound is obtained as purplish blue needle-like crystals having the following physical properties.

(1) The compound exhibits molecular peak of $M^+=302.1280$ (calculated molecular weight is 302.1266 as $C_{16}H_{18}N_2O_4$).

(2) The compound exhibits a purplish blue single spot of Rf value of 0.80 by the same silica gel thin layer chromatography as described in Example 1 (10-decarbamoyloxy-9-dehydro-mitomycin B exhibits Rf value of 0.70 in the same condition).

Figure 3:
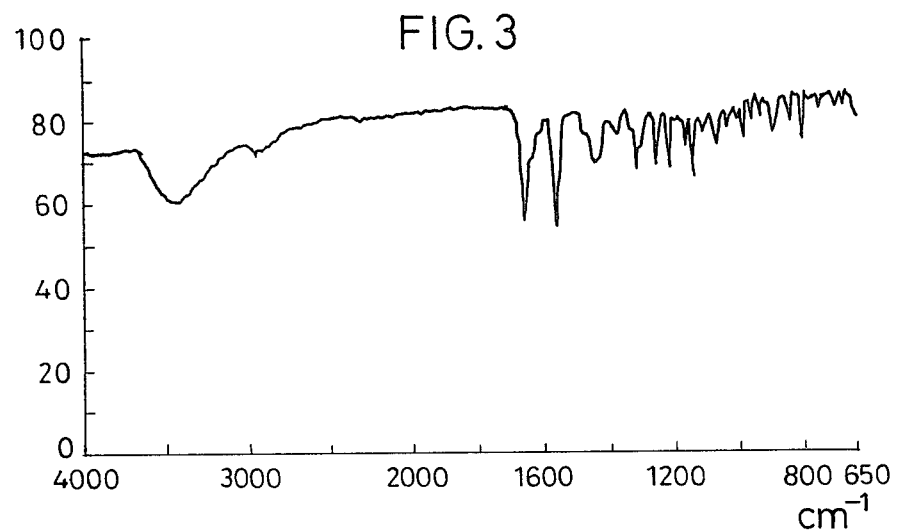

(3) IR spectrum (KBr tablet) as shown in FIG. 3.

(4) Chemical shift of proton by 60 MHz NMR using tetramethylsilane as internal standard and chloroform-D as a measuring solvent is shown by $\delta$(ppm): 6.32(s, 1H), 5.50(s, 1H), 3.07(s, 3H), 2.25(2H), 2.22(s, 3H), 4.08(d, 1H), 3.41(dd, 1H), 1.85(s, 3H), 4.08(s, 3H).

EXAMPLE 4

Preparation of 7-amino-9a-O-methyl-10-decarbamoyloxy-9-dehydro-7-demethoxy-mitomycin B (Compound IV)

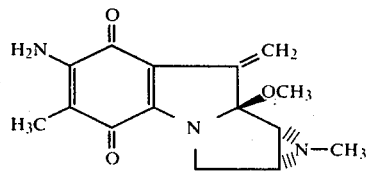

In this example, 10 mg of 9a-O-methyl-10-decarbamoyloxy-9-dehydro-mitomycin B is added to 5 ml of methanol saturated with ammonia. The mixture is stirred at room temperature for 18 hours, and then concentrated to dryness under reduced pressure. The residue is crystallized from acetone and petroleum ether to obtain 6.2 mg of the desired compound (yield 65.2%) as green needle-like crystals.

(1) The compound exhibits molecular peak of $M^+=287.1252$ (calculated molecular weight is 287.1269 as $C_{15}H_{17}N_3O_3$).

(2) The compound exhibits a deep green single spot of Rf value of 0.63 by the same silica gel thin layer chromatography as described in Example 1 (9a-O-methyl-10-decarbamoyloxy-9-dehydro-9a-dehydroxy-mitomycin B exhibits Rf value of 0.80 in the same condition).

Figure 4:
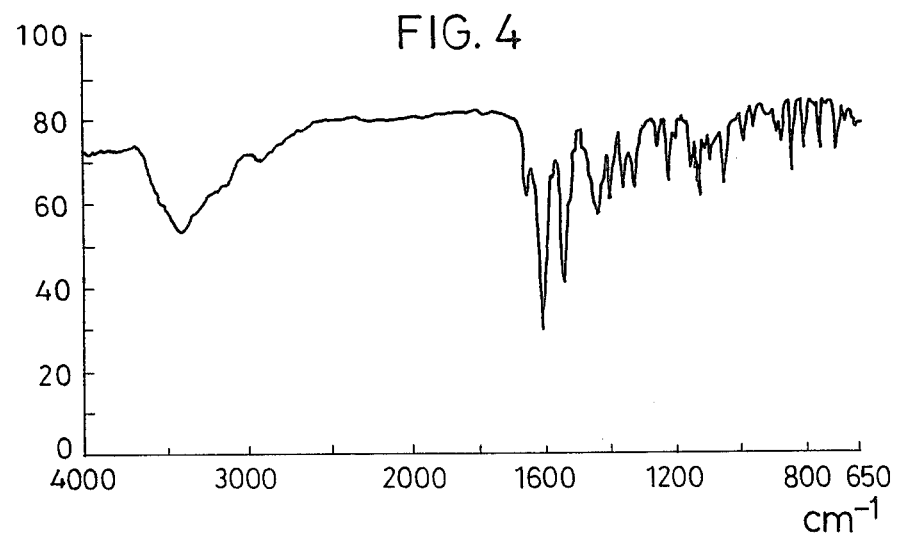

(3) IR spectrum (KBr tablet) as is shown in FIG. 4.

(4) Chemical shift of proton by 100 MHz NMR using tetramethylsilane as internal standard and methanol-$D_4$ as a measuring solvent is shown by $\delta$(ppm): 6.08(d, 1H), 5.34(d, 1H), 3.06(s, 3H), 2.43(2H), 2.21(s, 3H), 4.26(d, 1H), 3.43(dd, 1H), 1.77(s, 3H), 4.81(exchange with $CD_3OD$).

EXAMPLE 5

Preparation of 7-amino-9a-O-methyl-10-decarbamoyloxy-9-dehydro-7-demethoxy-mitomycin B (Compound IV) by fermentation.

In this example, *Streptomyces caespitosus* ATCC 27422 is used as a seed strain. One loopful of the strain is inoculated in 50 ml of a first seed medium in a 250 ml Erlenmeyer flask. Culturing is carried out at 28° C. for 2 days. The first culture is then transferred to a 2 l-Erlenmeyer flask with baffles containing 500 ml of a second seed medium. Culturing is carried out at 28° C. for 2 days. Then 1.5 l of the second culture (3 flasks) is transferred to a 200 l-culturing tank containing 100 l of a third seed medium. Culturing is carried out at 28° C. for 2 days with aeration and stirring (revolution: 250 r.p.m., aeration: 60 l/min.).

The first, second and third seed media comprise 15 g/l glucose, 5 g/l soluble starch, 10 g/l dry yeast, 5 g/l NaCl, 3 g/l $CACO_3$, pH 7.0 (before sterilization at 120° C. for 20 minutes).

Then, 100 l of the third culture is transferred to 2 Kl-fermentation tank containing 1 Kl of a fermentation medium comprising 15 g/l sucrose, 20 g/l soluble starch, 40 g/l soybean cake, 5 g/l NaCl, 200 mg/l $CoCl_2.6H_2O$, 5 ml/l normal paraffin pH 7.2 (before sterilization at 120° C. for 20 minutes).

Culturing is carried out at 28° C. for 5 days with aeration and stirring (revolution: 80 r.p.m., aeration: 400 l/min.).

After culturing, 20 Kg of sodium tetraborate ($Na_2B_4O_7.10H_2O$) is dissolved in the culture liquor and 100 Kg of Radiolite #600 (trade mark of a filtrate aid, made by Showa Kagaku Kogyo Co., Ltd., Japan), is added. The microbial cells are filtered off and the filtrate is passed through a column packed with 50 l of Diaion HP-20 (trade mark for an ion exchange resin, made by Mitsubishi Kasei Kogyo Co., Ltd., Japan). The resin is washed with 250 l of deionization water and elution is carried out with 250 l of 50% aqueous methanol and subsequently with 150 l of methanol. Then 200 l of the eluate containing the desired compound is concentrated under reduced pressure to about 26 l. About 8 Kg of sodium chloride is dissolved in the concentrate, and the concentrate is extracted 5 times each with 17 l of chloroform and the chloroform layers are combined and concentrated to 1 l. To the concentrated solution, anhydrous sodium sulfate is added to dehydrate the solution. The solution is then passed through a column packed with 7 l of silica gel. Elution is carried out with a mixed solvent of chloroform and methanol (100:1-5). Fractions of the eluate containing the desired compound are combined, concentrated and subjected to silica gel column chromatography using the same solvent system as above. Fractions containing the desired compound are concentrated and subjected to silica gel column chromatography using a mixed solvent of ethyl acetate and acetone (100:1); and this chromatography is then repeated. The thus obtained fractions containing the desired product are concentrated and subjected to alumina column chromatography using a mixed solvent of chloroform and acetone (98:2). The eluate is concentrated to dryness and the residue is crystallized from acetone and petroleum ether to obtain 1.9 mg of the desired compound as green needle-like crystals having the following physical properties, (1) Melting point about 270° C.; (browning at about 220° C.).

(2) Mass spectrum: Calculated as $C_{15}H_{17}N_3O_3$ 287.1269. Found 287.1252.

(3) PMR spectrum (in $CD_3OD$): 1.77(s, 3H), 2.21(s, 3H), 2.44(bs, 2H), 3.06(s, 3H), 3.42(dd, 1H), 4.26(d, 1H), 5.34(d, 1H), 6.07(d, 1H).

(4) Electronic absorption spectrum (in MeOH): 222 nm (log ε 4.02), 289(4.03), 373(4.25), 602(2.37).

(5) IR spectrum (KBr tablet): coincides with FIG. 4.

(6) Rf value by TLC (thin layer chromatography):

TABLE 2

| | TLC by silica gel (art 5714 made by Merck & Co.) | | |
|---|---|---|---|
| | Developer | | |
| Antibiotic | Chloroform: Methanol (9:1) | Ethyl acetate: Acetone (6:4) | Chloroform: Acetone (6:4) |
| Mitomycin A | 0.40 | 0.46 | 0.14 |
| Mitomycin B | 0.31 | 0.48 | 0.19 |
| Mitomycin C | 0.21 | 0.24 | 0.05 |
| Mitomycin D | 0.14 | 0.24 | 0.05 |
| Mitomycin E | 0.30 | 0.33 | 0.11 |
| Porfiromycin | 0.36 | 0.48 | 0.16 |
| Compound IV | 0.74 | 0.77 | 0.60 |
| Compound I | 0.70 | 0.79 | 0.67 |
| Compound II | 0.93 | 0.82 | 0.77 |

TABLE 3

| | TLC by alumina (art 5731, made by Merck & Co.) | | |
|---|---|---|---|
| | Developer | | |
| Antibiotic | Chloroform: Methanol (9:1) | Ethyl acetate: Acetone (6:4) | Chloroform: Acetone (6:4) |
| Mitomycin A | 0.56 | 0.21 | 0.08 |
| Mitomycin B | 0.40 | 0.14 | 0.04 |
| Mitomycin C | 0.28 | 0.09 | 0.02 |
| Mitomycin D | 0.12 | 0.05 | 0.01 |
| Mitomycin E | 0.46 | 0.21 | 0.07 |
| Porfiromycin | 0.47 | 0.29 | 0.08 |
| Compound IV | 0.75 | 0.76 | 0.67 |
| Compound I | 0.72 | 0.73 | 0.58 |
| Compound II | 0.83 | 0.84 | 0.84 |

| (7) Elementary analysis (as $C_{15}H_{17}N_3O_3$): | | | |
|---|---|---|---|
| | H | C | N |
| Found (%) | 5.95 | 62.73 | 14.34 |
| Calculated (%) | 5.96 | 62.70 | 14.63 |

(8) Specific rotation: Measurement was impossible as the compound is deep green.

(9) Distinction of basic, acidic or neutral property: Neutral.

(10) Solubility: Soluble in methanol, ethanol, acetone, ethyl acetate and chloroform, very slightly soluble in benzene, ethyl ether and water, insoluble in n-hexane.

From the foregoing physical properties, the compound is identified as 7-amino-9a-O-methyl-10-decarbamoyloxy-9-dehydro-7-demethoxy-mitomycin B.

EXAMPLE 6

Production of 10-decarbamoyloxy-9-dehydro-mitomycin B (Compound I) by fermentation In this example, the same seed media (first, second and third media) and fermentation medium as described in Example 5 are used.

One loopful of Streptomyces caespitosus ATCC 27422 is inoculated in 50 ml of the seed medium in a 250 ml-Erlenmeyer flask and culturing is carried out at 28° C. for 2 days. Second and third seed culturing are carried out in the same manner as described in Example 5. Then all of the third seed culture is transferred in a 2 Kl-fermentation tank containing 1 Kl of a fermentation medium and main fermentation is carried out in the same manner as described in Example 5.

After the completion of fermentation, a concentrated extract with chloroform is obtained in a same manner as described in Example 5. The extract is dehydrated with anhydrous sodium sulfate and passed through a column packed with alumina. Elution is carried out with chloroform. Fractions containing the desired compound are combined and concentrated, and the concentrate is allowed to stand overnight in a refrigerator. A deposited precipitate is then filtered off and the filtrate is concentrated under reduced pressure. A small amount of chloroform is added to the residue and insoluble materials are filtered off. The filtrate is then subjected to silica gel column chromatography using a mixed solvent of chloroform and acetone (10:0-3). Fractions containing the desired compound are combined and concentrated. The concentrate is again subjected to the same silica gel column chromatography as above. Fractions containing the desired compound are combined and concentrated. The concentrate is crystallized from acetone to obtain 5.6 mg of purplish black needle like crystals having the following physical properties.

(1) Melting point: about 125° C.

(2) Mass spectrum: Calculated as $C_{15}H_{16}N_2O_4$ 288.1110. Found 288.1135.

(3) PMR spectrum (in $CD_3OD$): 1.84(s, 3H), 2.21(s, 3H), 2.44(bs, 2H), 3.46(dd, 1H), 4.02(s, 3H), 4.03(d, 1H), 5.48(d, 1H), 6.09(d, 1H).

(4) Electronic adsorption spectrum (in MeOH): 226 nm (log ε 4.08), 291(4.03), $324^{sh}$(3.93), 578(3.04).

(5) IR spectrum (KBr tablet): coincides with FIG. 1.

(6) Rf value by TLC is exhibited in Tables 2 and 3.

| (7) Elementary analysis (as $C_{15}H_{16}N_2O_4$): | | | |
|---|---|---|---|
| | H | C | N |
| Found (%) | 5.64 | 62.34 | 9.37 |
| Calculated (%) | 5.59 | 62.49 | 9.72 |

(8) Specific rotation: Measurement was impossible as the compound is purplish black.

(9) Distinction of acidic, basic or neutral property: Neutral.

(10) Solubility: Soluble in methanol, ethanol, acetone, ethyl acetate and chloroform, very slightly soluble in benzene, ethyl ether and water, insoluble in n-hexane.

From the foregoing properties, the compound is identified as 10-decarbamoyloxy-9-dehydro-mitomycin B (Compound I).

EXAMPLE 7

Production of 9a-O-methyl-10-decarbamoyloxy-9-dehydro-mitomycin B (Compound II) by fermentation In this example, the same seed media (first, second and third seed media) and fermentation medium as described in Example 5 are used. Culturing is also carried out in the same manner as described in Example 5.

After the completion of culturing, a concentrated extract with chloroform is obtained in the same manner as described in Example 5. Anhydrous sodium sulfate is then added to the extract for dehydration. The resultant extract is passed through a column packed with alumina and elution is carried out with chloroform. Fractions containing the desired compound are combined and concentrated. The concentrate is allowed to stand overnight in a refrigerator. A deposited precipitate is filtered off and the filtrate is concentrated under reduced pressure. A small amount of chloroform is then added to the residue and insoluble materials are filtered off. The filtrate is subjected to silica gel column chromatography using a mixed solvent of chloroform and acetone (4:1 to 3:2). Fractions containing the desired compound are combined and concentrated. The concentrate is again subjected to silica gel column chromatography using a mixed solvent of chloroform and acetone (49:1 to 9:1). Fractions containing the desired compound are combined and concentrated. The concentrate is then subjected to alumina column chromatography using a mixed solvent of benzene and ethyl acetate (95:5) as a developer. The filtrate is concentrated to dryness and the residue is crystallized from n-hexane to obtain 2.8 mg of purplish blue needle-like crystals having the following physical properties.

(1) Melting point: 92° to 93° C.

(2) Mass spectrum: Calculated as $C_{16}H_{18}N_2O_4$ 302.1266. Found 302.1279.

(3) PMR spectrum (in $CD_3OD$): 1.85(s, 3H), 2.21(s, 3H), 2.46(bs, 2H), 3.05(s, 3H), 3.38(dd, 1H), 4.02(s, 3H), 4.07(d, 1H), 5.44(d, 1H), 6.21(d, 1H).

(4) Electronic absorption spectrum (in MeOH): 220 nm (log ε 4.15), 289(4.05), 320(4.00), 569(3.08).

(5) IR spectrum (KBr tablet): coincides with FIG. 3.

(6) Rf values in thin layer chromatography are shown in Tables 2 and 3.

| (7) Elementary analysis (as $C_{16}H_{18}N_2O_4$): | | |
|---|---|---|
| H | C | N |
| Found (%) 5.99 | 63.29 | 8.88 |
| Calculated (%) 6.00 | 63.56 | 9.27 |

(8) Specific rotation: Measurement was impossible as the compound is purplish blue.

(9) Distinction of acidic, base or neutral properties: neutral.

(10) Solubility: Soluble in methanol, ethanol, acetone, ethyl acetate, chloroform, benzene, ethyl ether and n-hexane, very slightly soluble in water.

From the foregoing, the compound is identified as 9a-O-methyl-10-decarbamoyloxy-9-dehydro-mitomycin B (Compound II).

What is claimed is:

1. A mitomycin derivative represented by the formula

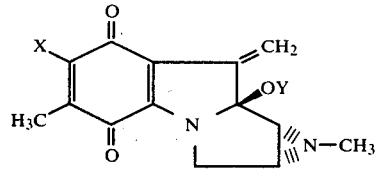

wherein X is a $C_1$–$C_4$ alkoxy group or $NH_2$ and Y is hydrogen or a $C_1$–$C_4$ alkyl group.

2. A mitomycin derivative of claim 1 wherein X is a methoxy group and Y is hydrogen.

3. A mitomycin derivative of claim 1 wherein X is a methoxy group and Y is a methyl group.

4. A mitomycin derivative of claim 1 wherein X is $NH_2$ and Y is hydrogen.

5. A mitomycin derivative of claim 1 wherein X is $NH_2$ and Y is a methyl group.

* * * * *